United States Patent [19]

Park

[11] 4,450,274

[45] May 22, 1984

[54] PREPARATION OF ETHAMBUTOL-DIISONIAZIDE METHANE SULFONIC ACID SALT

[75] Inventor: Sang-Woo Park, Seoul, Rep. of Korea

[73] Assignee: Korean Advanced Institute of Science and Technology, Seoul, Rep. of Korea

[21] Appl. No.: 387,037

[22] Filed: Jun. 10, 1982

[30] Foreign Application Priority Data

Jul. 7, 1981 [KR] Rep. of Korea ............................ 2455

[51] Int. Cl.$^3$ ............................................. C07D 401/12
[52] U.S. Cl. ....................................... 546/262; 546/324
[58] Field of Search ................................ 546/262, 324

[56] References Cited

U.S. PATENT DOCUMENTS 3,718,655  2/1973  Ferrer-Salat et al. ............... 546/324

Primary Examiner—Henry R. Jiles
Assistant Examiner—Bernard Dentz
Attorney, Agent, or Firm—Burns Doane, Swecker & Mathis

[57] ABSTRACT

This invention pertains to a new process for preparing an ethambutol-sulfonic acid derivative which is widely used as an antituberculosis agent. In the known process, there are many defects which include: side reactions, impurities, low yield, high cost production inefficiency and pollution hazard.

For the purpose of preparing an ethambutol-sulfonic acid derivative of a higher purity and higher yield than the known process, ethambutol or its hydrogen chloride salt is reacted with chloromethane sulfonic acid or its sodium salt in the lower alcoholic solvent such as methanol, ethanol, propanol, or isopropanol, at a temperature between room temperature and boiling point of the solvent, for about an hour, to produce ethambutol-chloromethane-sulfonate which is then reacted with isoniazid to produce the ethambutol-sulfonic acid derivative of the present invention.

10 Claims, No Drawings

PREPARATION OF ETHAMBUTOL-DIISONIAZIDE METHANE SULFONIC ACID SALT

FIELD OF THE INVENTION

This invention relates to a synthetic process of medical and organic chemistry fields.

Up to now, many antituberculosis agents have been widely known including para-aminosalicylates, ethambutol-isoniazid-methane sulfonates, antibiotics and other complex agents.

This invention relates to a new, useful and improved process for preparing an ethambutol-sulfonic acid derivative as compared to the processes of the prior art.

BACKGROUND OF THE INVENTION

The known process for preparing ethambutol-isoniazid-methane sulfonates is disclosed in No. 2036935 in the German Patent Gazette for Public Inspection. In the prior art isoniazid-methane sulfonic acid or its sodium salt is produced through reaction in water, and separated and purified and then this reacted with ethambutol in alcoholic solvents such as methanol or ethanol, to produce ethambutol-isoniazid-methane sulfonate.

However, in this process, if isoniazid-methane-sulfonic acid or its sodium salt is reacted with ethambutol without any separation, this method results in a low yield of the final products e.g. 60% and high cost.

Furthermore, it is time-consuming to separate or crystallize the ethambutol-isoniazid-methane sulfonate.

Moreover, in the prior art technique as set forth above, it is impossible to obtain an ethambutol-isoniazid-methane sulfonates having a satisfactorily high activity.

In order to overcome these disadvantages, present the invention relates to an improved process for preparing ethambutol-isoniazid-methane sulfonate.

BRIEF DESCRIPTION OF THE INVENTION

An object of the present invention is to prepare ethylene diimino dibutanol (i.e. ethambutol)-isoniazid-methane sulfonate in an improved process.

In the prior art, the final product is produced in alcoholic solvent after the intermediate is separated and purified.

But, in this invention, ethambutol or its hydrogen chloride salt is reacted in alcoholic solvent with chloro methane sulfonic acid or its sodium salt which can be easily produced from dichloro methane and sodium sulfide ($Na_2SO_3$) to produce ethambutol-chloromethane sulfonate and then reacted without any separation with isoniazid to produce ethambutol-isoniazid-methane sulfonate.

Summarized briefly, the most important innovation of this invention is that, without any separation of ethambutol-chloromethane sulfonate, this reaction intermediate is reacted directly with isoniazid to produce ethambutol-isoniazid-methane sulfonate.

DETAILED DESCRIPTION OF THE INVENTION

The present invention relates to a new process for preparing ethambutol-sulfonic acid derivative which is used as an antituberculosis agent.

More specifically, this invention relates to a new process for preparing d(+)2,2'-(ethylene diimino) dibutanol-diisoniazid-methane sulfonate of the following general formula(I) in which ethambutol of the following general formula(II) or its hydrogen chloride salt is reacted with chloro-methane sulfonic acid of the following general formula(III) or its sodium salt to produce ethambutol-chloro-methane sulfonate of the following general formula (IV) as an intermediate without any separation, this intermediate is reacted with isoniazid of the following general formula(V).

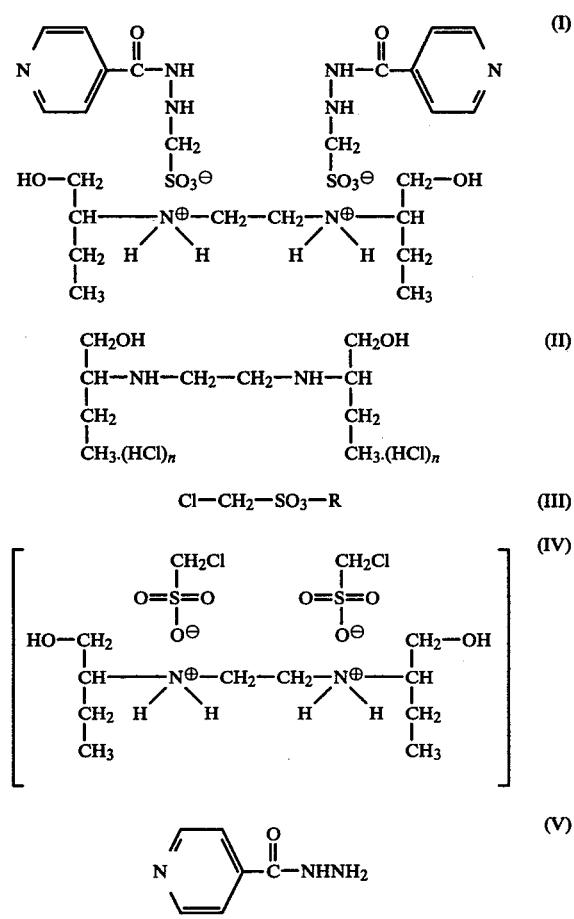

Wherein n represents 0 or 1, and R represents a hydrogen atom or a sodium atom.

Heretofore the known process for producing ethambutol-isoniazid-methane sulfonate (which is disclosed in German Gazette Patent Number for Public Inspection 2,036,935) is that isoniazid-methane sulfonic acid of the following general formula(VI) or its sodium salt is produced through reaction in water, subjected to separation and purification, and reacted with ethambutol in alcoholic solvents such as methanol or ethanol to produce the following ethambutol-isoniazid-methane sulfonate:

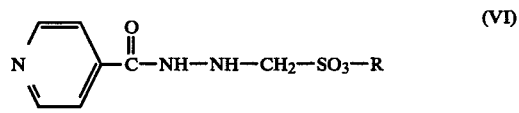

wherein, R represents the same as the above.

However, in the known process the production yield is isoniazid-methane sulfonic acid or its sodium salt is as low as 60%, and also the known process has some disadvantages for industrialization due to a possibility of air pollution when sulfuric acid gas is produced.

Also, the isoniazid-methane sulfonic acid must undergo separation and refining before it is reacted with ethambutol in alcoholic solvent such as methanol or ethanol to produce ethambutol-isoniazid-methane sulfonate.

In the above known process, if isoniazid-methane sulfonic acid or its sodium salt is not refined before it is reacted with ethambutol, then much side reaction and impurities are produced and the yield is reduced to 60%.

Further, the separation or recrystallization step of ethambutol-isoniazid-methane sulfonate takes a long time and the production process is delayed and the manufacturing cost increased so that the known process is not economically feasible.

With an aim to invent a new and advanced process for producing ethambutol-isoniazid-methane sulfonate which is industrially feasible and has no pollution problem apart from the known process, through long research and test, the present inventor has found that ethambutol or its hydrogen chloride salt is reacted with chloro-methane sulfonic acid or its sodium salt to produce ethambutol-chloro-methane sulfonate which, without any separation, is reacted with isoniazid to produce ethambutol-isoniazid-methane sulfonate within 1 hour.

More detailed explanation of the present invention is as follows:

Ethambutol of general formula(II) or its hydrogen chloride salt is reacted with chloro-methane sulfonic acid of general formula(III) in an alcoholic solvent containing 1-4 carbon atoms such as methanol, ethanol, propanol, or isopropanol. Ethambutol chloro-methane sulfonate of general formula(IV) is produced, and, without any separation, isoniazid of general formula(V) is added to this reaction solution and heated at between room temperature and the boiling temperature of the solvent.

Within an hour, the desired ethambutol-isoniazid-methane sulfonate of general formula(I) is produced. In this process, chloro-methane sulfonic acid and isoniazid should be added 2 moles each to 1 mole of ethambutol. When isoniazid of general formula(V) is added to this reaction solution, the addition of a small quantity of alkaline activated alumina improves the production yield.

The reaction in which free base of ethambutol of general formula(II) and chloro-methane sulfonic acid of general formula(III) are reacted to produce ethambutol-chloro-methane sulfonate of general formula(IV) takes place quite easily at low temperature, i.e., room temperature, but in order to improve the purity and yield of the product it is desirable to keep heating and refluxing at the boiling temperature of the solvent which is being used.

In a preferred embodiment, the reaction between hydrogen chloride salt of ethambutol and sodium salt of chloro-methane sulfonic acid should be carried out in an autoclave, and the reaction temperature maintained at 100°–110° C.

At the end of the reaction, sodium chloride formed should be removed by filtration, and isoniazid of general formula(V) is added to the filtrate and reacted for 20–30 minutes to produce easily ethambutol-isoniazid-methane sulfonate of general formula(I).

The preparation of chloro-methane sulfonic acid or its sodium salt which is used as a starting material in the present reaction is well-known to one skilled in the art and can be easily produced from dichloromethane and sodium sulfite.

The new process for producing ethambutol-isoniazid-methane sulfonate is as mentioned above, and it is assumed that a chemical reaction mechanism is as follows:

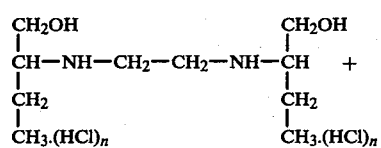

(II)

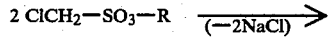

(III)

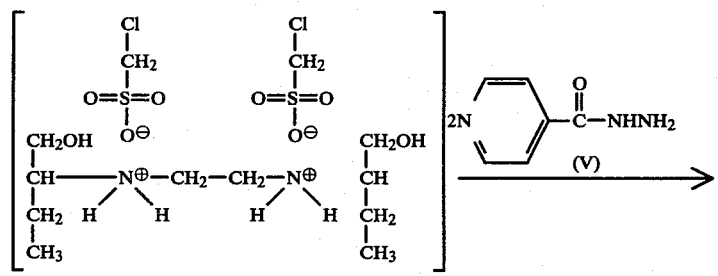

(IV)

$$\left[\begin{array}{c}\text{structure shown}\end{array}\right]$$

(I)

Wherein, n and R represent the same as above.

The key to the present invention is that, without any separation of ethambutol-chloro-methane sulfonate of general formula(IV) as prepared by the reaction of ethambutol with chloro-methane sulfonic acid, this compound is reacted directly with isoniazid of general formula(V) to produce ethambutol-isoniazid-methane sulfonate of general formula(I).

In the following examples, the present invention is explained more specifically; however, the above description and illustrations should not be construed as limiting the scope of the invention as described by the appended claims.

EXAMPLE 1

20.4 g (0.1 mole) of ethambutol and 28.6 g (0.2 mole) of chloro-methane sulfonic acid is suspended in 180 ml of anhydrous methanol, and the solution is heated and refluxed for 30 minutes.

To this solution, a mixture of 27.4 g (0.2 mole) of isoniazid and 70 ml of anhydrous methanol are added dropwise at the same temperature for 10 minutes, and then the solution is heated and stirred for another 20 minutes.

At the end of reaction, the reaction solution is cooled to room temperature and 30 ml of cyclohexane is added to this solution and then white powder is precipitated. It is filtered and recrystallized in ethanol, and then 47.4 g of white ethambutol-isoniazid-methane sulfonate are obtained.

theoretical yield: 71%.
melting point: 121°–122.5° C.
U.V. spectrum(ethanol): 237 nm(min), 265 nm(max).
I.R. spectrum(KBr disc) (cm$^{-1}$): 3500–2800, 3150, 1640, 1530, 1440, 1300, 1160, 1030.
N.M.R. spectrum (D$_2$O) (δ-ppm): 8.8(d,4H), 7.8(d,4H), 4.32(S,4H), 3.8(S,4H), 4.5–3.3(m,6H), 1.9(q,4H), 1.2(t,6H).

EXAMPLE 2

27.2 g (0.1 mole) of ethambutol-2HCl and 33 g (0.2 mole) of chloro-methane sulfonic acid-sodium salt are suspended in 230 ml of anhydrous methanol in an autoclave and heated for 1 hour maintaining the inside temperature at 100°–105° C.

Then the reaction solution is cooled to room temperature and sodium chloride formed is removed by filtration.

Under the same reaction condition as in Example 1, 27.4 g (0.2 mole) of isoniazid are added to the filtrate.

Then 45.3 g of white crystalline ethambutol-isoniazid-methane sulfonate are obtained.

m.p.: 121°–122° C.
yield: 68% (theoretical).

U.V., I.R., and N.M.R. spectrum of the product are the same as in Example 1.

EXAMPLE 3

20.4 g (0.1 mole) of ethambutol and 28.6 g (0.2 mole) of chloro-methane sulfonic acid are suspended in anhydrous ethanol in a reaction flask, and stirred for 30 minutes with heating under refluxing conditions.

To this solution, 27.4 g (0.2 mole) of isoniazid are added and after 30 minutes continuous stirring with heating under reflux, the insolubles are removed by filtration and then solution is cooled.

After filtration and drying of the produced white crystal, 58 g of ethambutol-isoniazid-methane sulfonate are obtained.

m.p.: 121°–122.5° C.
yield: 87%.

U.V., I.R., and N.M.R. spectrum of the product are the same as in Example 1.

EXAMPLE 4

27.7 g (0.1 mole) of ethambutol-2HCl and 33 g (0.2 mole) of chloro methane sulfonic acid-sodium salt are suspended in 250 ml of anhydrous ethanol in an autoclave and heated for 1 hr. at 105° C.

Then the reaction solution is cooled to room temperature and sodium chloride formed is removed by filtration. Under the same reaction condition as in Example 3, 27.4 g (0.2 mole) of isoniazid are added to the filtrate.

Then 50.7 g of white crystalline ethambutol-isoniazid-methane sulfonate is obtained.

m.p.: 121°–122.5° C.
yield: 76%.

U.V., I.R. and N.M.R. spectrum of the product are the same as in Example 1.

EXAMPLE 5

To the reaction flask equipped with reflux condenser, 20.4 g (0.1 mole) of ethambutol, 28.6 g (0.2 mole) of chloro-methane sulfonic acid, and 150 ml of anhydrous propanol are added and heated under reflux for 30 minutes.

Then 27.4 g (0.2 mole) of isoniazid are added and stirred under reflux for another 30 minutes.

The reaction solution is cooled to room temperature and 50 ml of hexane are added.

White powder is formed and, after filtration and recrystallization from ethanol, 48 g of ethambutol-isoniazid-methane sulfonate are obtained.

m.p.: 121°-122° C.

yield: 72%.

U.V., I.R. and N.M.R. spectrum of the compound are the same as in Example 1.

EXAMPLE 6

27.7 g (0.1 mole) of ethambutol-2HCl and 33 g (0.2 mole) of chloro-methane sulfonic acid sodium salt are suspended in 200 ml of anhydrous propanol in an autoclave and heated for 1 hour at 105°-110° C.

The reaction solution is cooled to room temperature and sodium chloride formed is removed by filtration. Under the same reaction conditions as in Example 5, 27.4 g (0.2 mole) of isoniazid are added to the filtrate.

Then 42.7 g of white crystalline ethambutol-isoniazid-methane sulfonate are obtained.

m.p.: 121°-122° C.

yield: 64%.

U.V., I.R. and N.M.R. spectrum of the product are the the same as in Example 1.

EXAMPLE 7

To the reaction flask equipped with reflux condenser 20.4 g (0.1 mole) of ethambutol, 28.6 g (0.2 mole) of chloro-methane sulfonic acid, and 170 ml of anhydrous propanol are added and heated under refluxing conditioned for 30 minutes.

Then 27.4 g (0.2 mole) of isoniazid is added and stirred under reflux for another 30 minutes.

The reaction solution is cooled to room temperature and 30 ml of petroleum ether is added.

Then white powder is formed which is filtered and recrystallized from ethanol; 49.4 g of white crystalline ethambutol-isoniazid-methane sulfonate is obtained.

m.p.: 121-122 C.

U.V., I.R. and N.M.R. spectrum of the product are the same as in Example 1.

EXAMPLE 8

27.7 g (0.1 mole) of ethambutol-2HCl and 33 g (0.2 mole) of chloro-methane sulfonic acid sodium salt are suspended in 200 ml of anhydrous isopropanol in an autoclave and heated for 1 hour maintaining the reaction temperature at 105° C.

The reaction solution is cooled to room temperature and sodium chloride formed is removed by filtration.

Under the same reaction condition as in Example 7, 27.4 g (0.2 mole) of isoniazid are added to the filtrate.

Then 40.7 g of ethambutol-isoniazid-methane sulfonate are obtained.

m.p.: 121°-122° C.

yield: 61%.

U.V., I.R. and N.M.R. spectrum of the product are the same as in Example 1.

EXAMPLE 9

20.4 g (0.1 mole) of ethambutol and 28.6 g (0.2 mole) of chloro-methane sulfonic acid are suspended in 200 ml of anhydrous ethanol in reaction flask, and stirred for 30 minutes under reflux.

To this solution, 27.4 g (0.2 mole) of isoniazid and 3 g of alkaline activated alumina are added and stirred for another 30 minutes under reflux.

Then activated alumina is removed by filtration and 60.7 g of white crystalline ethambutol-isoniazid-methane sulfonate are obtained.

m.p.: 121°-122.5° C.

yield: 91%.

U.V., I.R. and N.M.R. spectrum of the compound are the same as the Example 1.

What is claimed is:

1. A process for preparing an d(+) 2,2-(ethylene diimino) dibutanol-diisoniazide-methane-sulfonate comprising reacting isoniazid with ethylene diimino dibutanol-chloro-methane sulfonate.

2. A process for preparing d(+) 2,2-(ethylene diimino) dibutanol-diisoniazide-methane-sulfonate according to claim 1, wherein the ethylene diimino dibutanol-chloro-methane sulfonate reactant is produced by reacting a chloro-methane sulfonic acid with a compound selected from the group consisting of ethylene diimino dibutanol and the hydrogen chloride salt thereof.

3. A process for preparing d(+) 2,2-(ethylene diimino) dibutanol-diisoniazide-methane sulfonate according to claim 2, wherein the chloro-methane-sulfonic acid is of the general formula

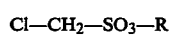

wherein R represents H or Na.

4. A process for preparing d(+) 2,2-(ethylenediimino) dibutanol-diisoniazide-methane sulfonate according to claim 1, wherein the reaction time is about one hour.

5. A process for preparing d(+) 2,2-(ethylene diimino) dibutanol-diisoniazide-methane sulfonate according to claim 1, wherein the reaction is carried out in the presence of alkaline activated alumina.

6. A process for preparing d(+) 2,2-(ethylene diimino) dibutanol-diisoniazide-methane sulfonate according to claim 1, wherein the reaction of the ethylene diimino dibutanol or its hydrogen chloride salt with the chloro-methane sulfonic acid is carried out in a solvent comprising a lower aliphatic alcohol containing not more than four carbon atoms, and wherein the reaction with isoniazid then is carried out without any separation.

7. A process for preparing d(+) 2,2-(ethylene diimino) dibutanol-diisoniazide-methane sulfonate according to claim 6, wherein the reaction of the ethylene diimino dibutanol-chloro-methane sulfonate with isoniazid is carried out at a temperature of between about room temperature and about the boiling temperature of the solvent.

8. A process for preparing d(+) 2,2-(ethylene diimino) dibutanol-diisoniazide-methane sulfonate according to claim 6, wherein the reaction of the ethylene diimino dibutanol hydrogen chloride salt with the chloro-methane sulfonic acid or its sodium salt is carried out at a temperature of between about 100° and about 110° C.

9. A process for preparing d(+) 2,2-(ethylene diimino) dibutanol-diisoniazide-methane sulfonate according to claim 7, wherein the reaction between isoniazid and ethylene diimino dibutanol-chloro-methane sulfonate proceeds for between about 20 and 30 minutes.

10. A process for preparing d(+) 2,2'-(ethylene diimino) dibutanol-diisoniazid-methane sulfonate comprising the steps of (a) reacting in alcohol under reflux conditions an ethylene diimino dibutanol of the formula
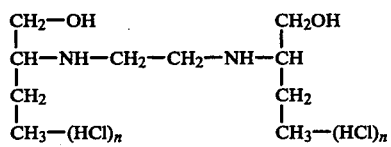
with a compound of the formula
$$Cl-CH_2-SO_3-R$$
wherein $R = Na$
(b) removing by filtration sodium chloride formed;
(c) adding isoniazid to the product of step (b); and
(d) heating the reaction mixture at 100°–110° C. for between about 20 and 30 minutes.
* * * * *